(12) United States Patent
McEwen et al.

(10) Patent No.: US 10,201,354 B1
(45) Date of Patent: Feb. 12, 2019

(54) TOURNIQUET SAFETY SLEEVE FOR REDUCING LIMB INJURY

(71) Applicant: Western Clinical Engineering Ltd., Vancouver (CA)

(72) Inventors: James Allen McEwen, Vancouver (CA); Michael Jameson, North Vancouver (CA); Tom Yu Chia Lai, Vancouver (CA)

(73) Assignee: Western Digital Engineering Ltd., Vancouver, B.C. (CA)

( * ) Notice: Subject to any disclaimer, the term of this patent is extended or adjusted under 35 U.S.C. 154(b) by 0 days.

(21) Appl. No.: 15/712,095

(22) Filed: Sep. 21, 2017

(51) Int. Cl.
*A61B 17/00* (2006.01)
*A61B 17/132* (2006.01)
*A61B 5/03* (2006.01)
*A61B 17/135* (2006.01)

(52) U.S. Cl.
CPC ............ *A61B 17/1325* (2013.01); *A61B 5/03* (2013.01); *A61B 17/135* (2013.01); *A61B 2562/0247* (2013.01)

(58) Field of Classification Search
CPC .............. A61B 17/132; A61B 17/1322; A61B 17/1325; A61B 17/135; A61B 17/1327; A61B 17/1355; A61F 13/00; A61F 13/00029; A61F 2013/00093; A61F 2013/00744

USPC ............................. 606/203; 424/443; 602/45
See application file for complete search history.

(56) References Cited

U.S. PATENT DOCUMENTS

| 6,525,238 | B2 * | 2/2003 | Corrales ................. A61F 15/00 600/499 |
| 6,988,992 | B2 * | 1/2006 | Just .................... A61B 5/02233 600/485 |
| 2007/0179421 | A1 * | 8/2007 | Farrow .................. A61H 9/005 602/75 |
| 2017/0079665 | A1 * | 3/2017 | Fellowes .............. A61B 17/132 |
| 2017/0112503 | A1 * | 4/2017 | Brown ............... A61B 17/1327 |
| 2018/0256173 | A1 * | 9/2018 | Seth .................... A61B 17/1327 |

* cited by examiner

*Primary Examiner* — Melanie R Tyson
(74) *Attorney, Agent, or Firm* — Klarquist Sparkman, LLP

(57) ABSTRACT

A sleeve for use with a tourniquet cuff to protect a patient's limb from tourniquet-related injury includes a stretchable body extending longitudinally over a sleeve length between a proximal end and a distal end. The body has a tubular shape, and the sleeve length is greater than a width of the tourniquet cuff. The body tapers from the proximal end to the distal end such that a proximal end circumference is greater than a distal end circumference. The body is formed to apply substantially uniform pressure to the patient's limb from the proximal end of the sleeve to the distal end of the sleeve varying only within a predetermined pressure range.

10 Claims, 15 Drawing Sheets

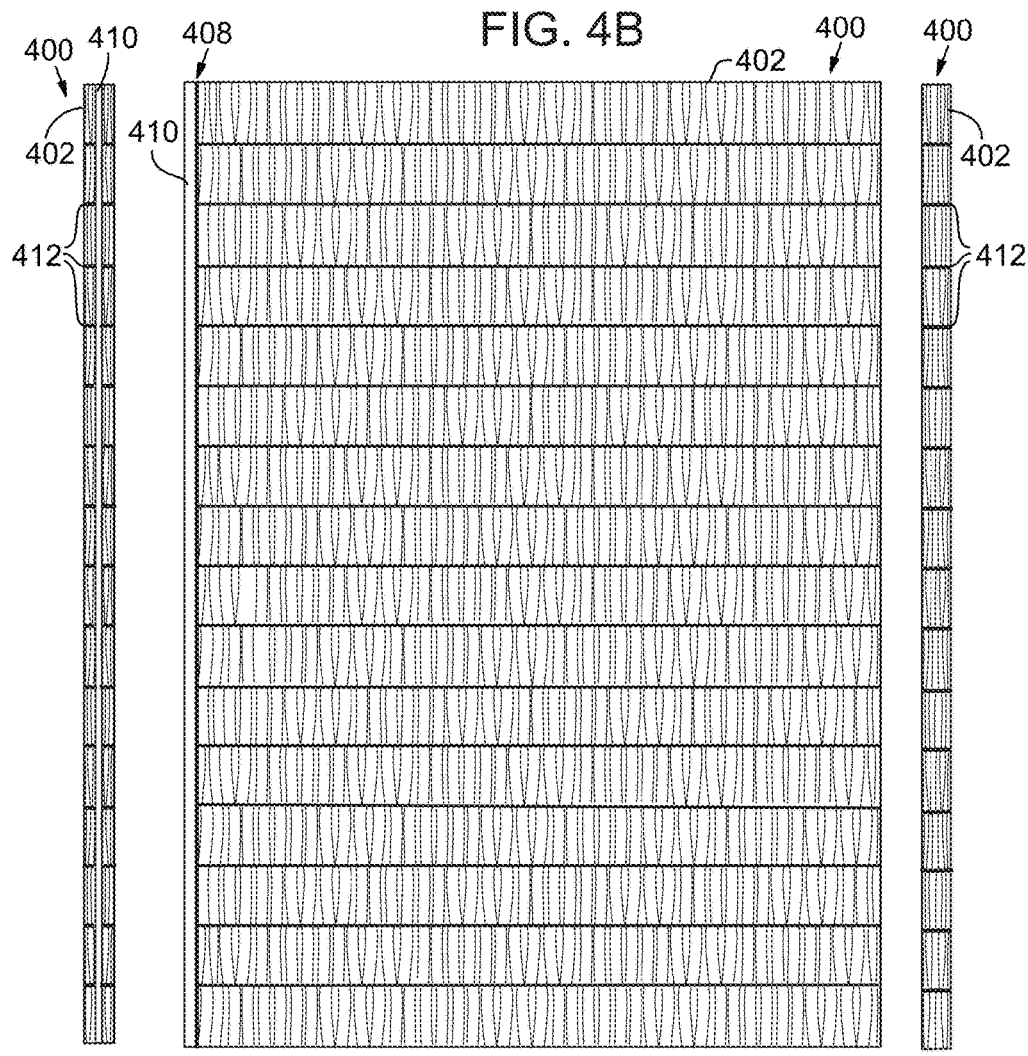

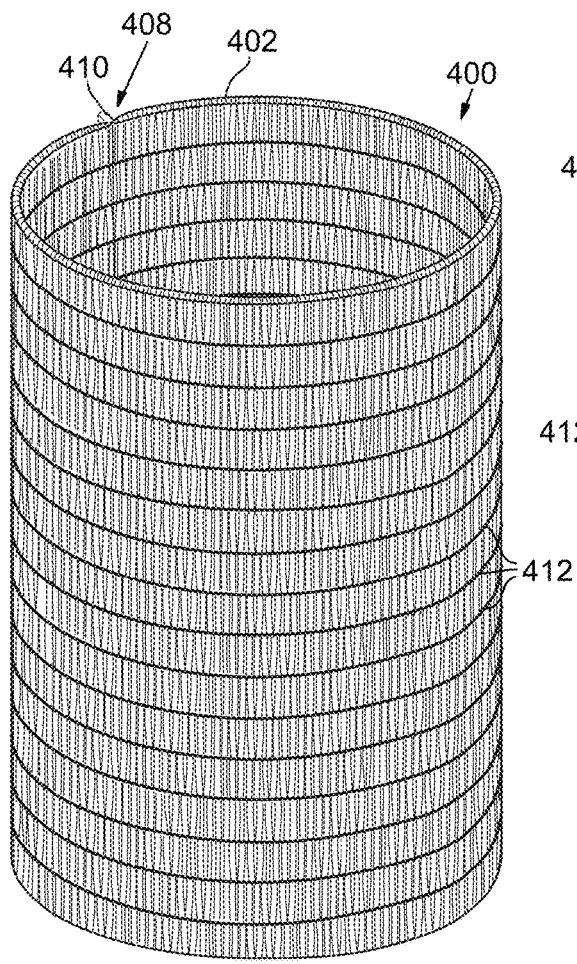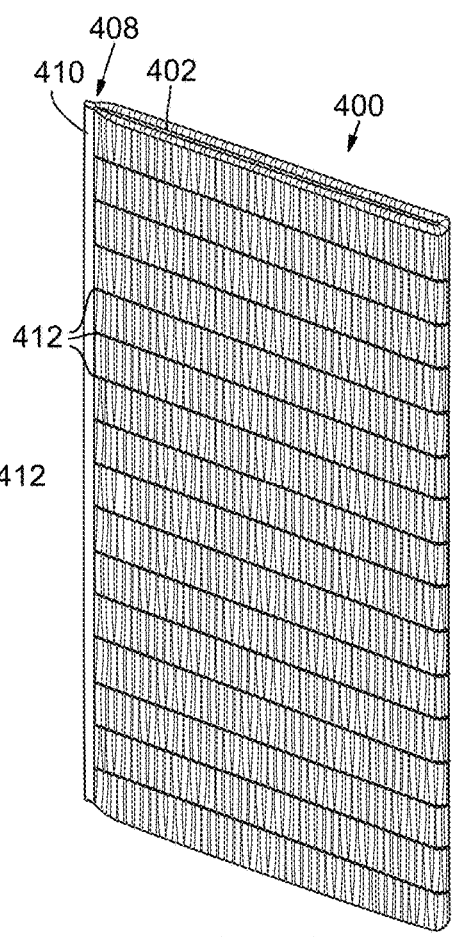
FIG. 4F
FIG. 4G

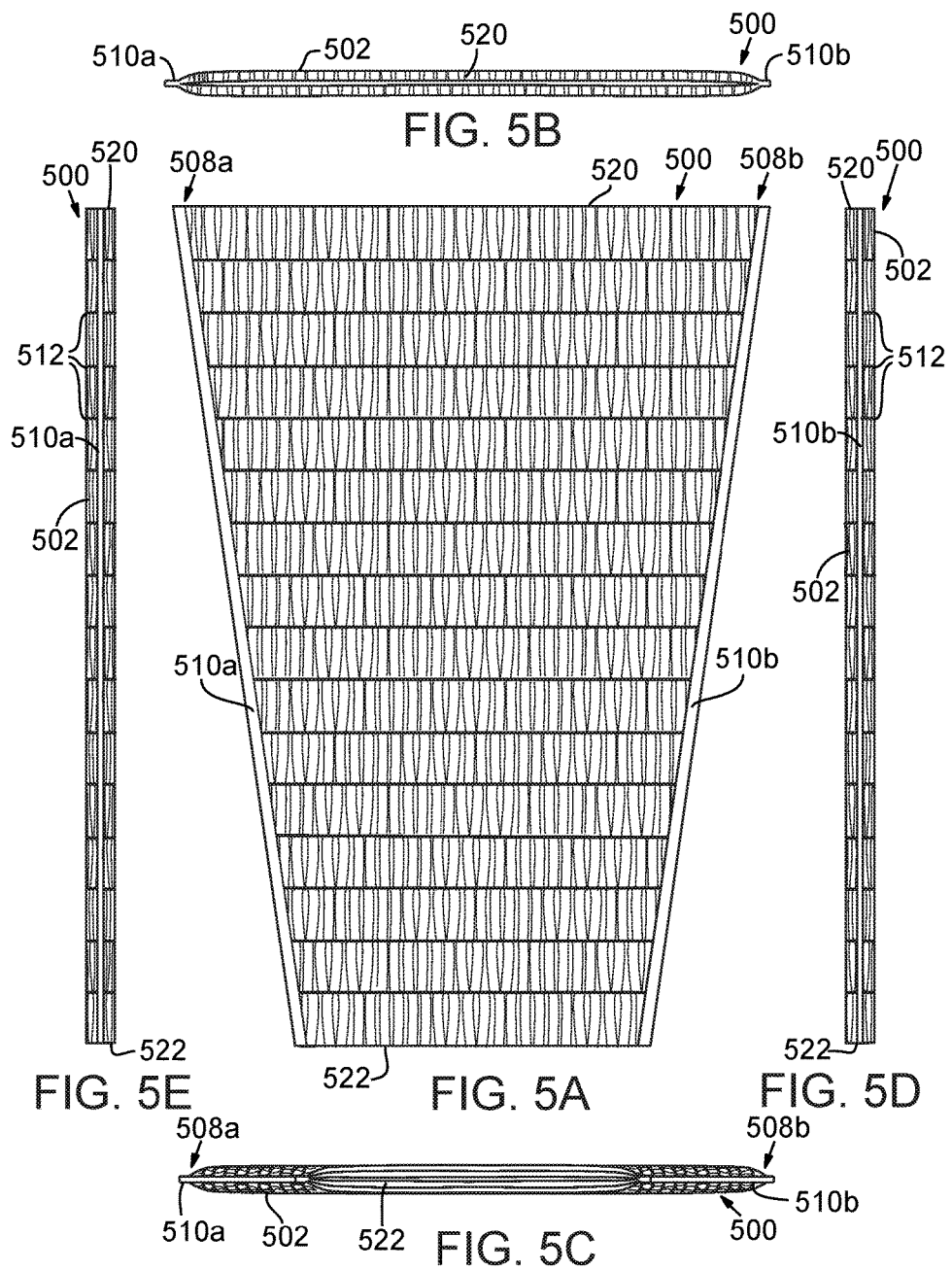

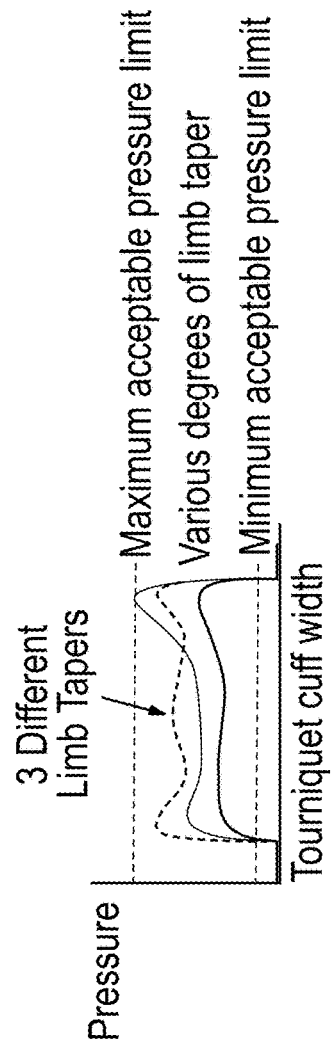
FIG. 11A
FIG. 11B

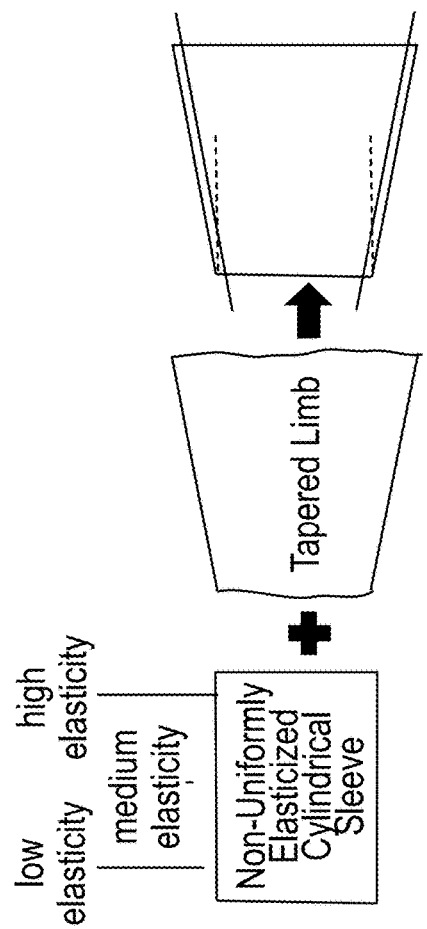
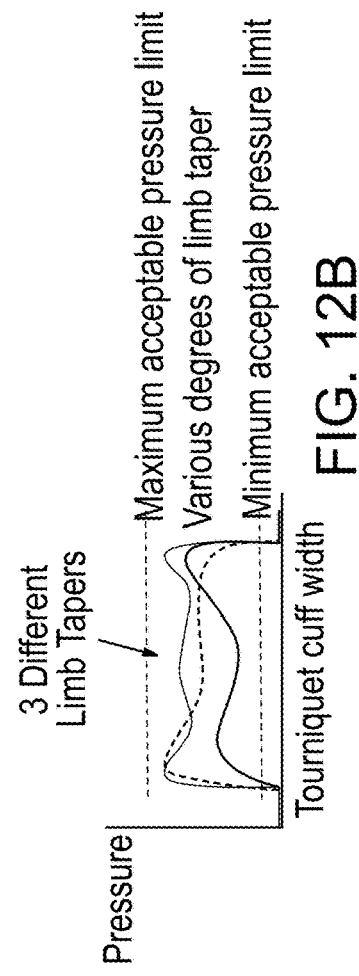
FIG. 12A
FIG. 12B

TOURNIQUET SAFETY SLEEVE FOR REDUCING LIMB INJURY

BACKGROUND

Surgical tourniquet cuffs typically are applied to a patient's limb at a desired location and are then pressurized in order to stop the flow of arterial blood past the cuff, thereby establishing a bloodless field in the portion of the limb distal to the cuff. The structure and function of some typical tourniquet cuffs of the prior art are described by Robinette-Lehmann U.S. Pat. No. 4,635,635, by Spence in U.S. Pat. No. 4,979,953 and by McEwen in U.S. Pat. Nos. 5,454,831 and 5,649,954. The pressure applied by such prior art tourniquet cuffs is typically controlled by electronic apparatus such as that described by McEwen in U.S. Pat. No. 4,469,099 and by McEwen and Jameson in U.S. Pat. No. 5,607,447.

The bloodless surgical field created by a pressurized tourniquet cuff facilitates many types of surgical procedures performed on upper limbs and lower limbs, helps improve the quality and consistency of the surgical procedures, reduces the need for blood transfusions, and shortens surgical times.

To reduce the probability of certain injuries to the soft tissues of the limb beneath a pressurized tourniquet cuff, some practitioners elect to apply a form of limb protection to the limb beneath the cuff. For example, in "Guideline for Care of Patients Undergoing Pneumatic Tourniquet-assisted Procedures," published by the Association of periOperative Registered Nurses (AORN) in the United States in 2015, it is noted that "[a] low-lint, soft padding (e.g., limb protection sleeve, two layers of stockinette) should be placed around the limb according to the cuff manufacturer's instructions for use. The padding should be wrinkle-free and should not pinch the skin."

In the prior art, soft bandages that have been used in conjunction with tourniquet cuffs have included sheet padding combined with a fluid-impervious layer and an adhesive tab as described by Hubbard in U.S. Pat. No. 4,406,281 as well as cast padding of the type wrapped around a broken limb before a cast is applied. Proper application of the soft bandages in conjunction with tourniquet cuff usage is very technique dependent, requiring a trained and experienced applicator. Further, some types of padding may release loose fibers when applied, and these fibers may enter the surgical field and may clog the hook-and-loop fasteners that are typically used to secure tourniquet cuffs in position around the limb, thereby reducing the effective strength of these fasteners and creating a potential hazard. Also, the padding itself may take on a non-uniform shape around the limb, especially when an overlying tourniquet cuff is inflated. Finally, if too much soft bandage is used or if it is applied improperly, then hazards may arise because the level of pressure required in the tourniquet cuff to stop blood flow past the cuff may increase substantially, and the position of the cuff on the limb may become unstable after inflation, increasing the likelihood that the cuff position may change significantly relative to the limb during use.

As an improvement to soft bandages and cast padding, tubular stockinette has also been used between the patient's limb and the tourniquet cuff. Typically, tubular stockinette is made and supplied in a wide range of predetermined "lay-flat" widths, knits and materials. Tubular stockinette consists of a knitted textile having a substantially cylindrical shape in which some of the knitted threads either are elastic or are knitted in a manner that permits elastic stretching of the tubular shape. In appearance, tubular stockinette resembles the ankle portion of a sock or the leg portion of a nylon stocking. Elastic threads are included in some types of tubular stockinette to give them stretch and elastic characteristics that are a function of the type and number of elastic and non-elastic threads used in the knit and the knit pattern itself. In other types of stockinette that are knitted from non-elastic threads, the stretch and elastic characteristics of the stockinette are primarily determined by the type of knit. Two general advantages of using tubular stockinette under a tourniquet cuff, in comparison to overlapping soft bandages, are (1) tubular stockinette does not shed loose fibers which can enter the surgical field and clog cuff fasteners, and (2) tubular stockinette does not produce as non-uniform a shape around the limb as can occur with soft bandages.

There are a number of limitations associated with such prior art tubular stockinette. The most important limitation is that the pressure applied to the encircled limb by the tubular stockinette may be too high or too low. If the tubular stockinette is stretched excessively to fit around the limb at the desired cuff location, too high a pressure may result. In such situations, the pressure applied to the limb by the elastically stretched tubular stockinette may be sufficiently high to stop the flow of venous blood out of the limb and impair the flow of arterial blood into the limb.

Such residual pressures are concerning, and manufacturers of cuffs and other tourniquet-related products emphasize that the deflated cuff and any underlying bandages should be completely removed as soon as tourniquet pressure is released, stating that even the slightest impedance of venous return may lead to congestion and pooling of blood in the operative field.

Alternatively, if the tubular stockinette is not stretched at all, or if it is not stretched sufficiently at a desired cuff location, then the tubular stockinette may apply no pressure to the underlying limb and inflation of an overlying tourniquet cuff may then produce folding and wrinkling of the tubular stockinette material. This can cause soft tissue injuries resulting from pinching, folding and shearing of skin beneath the tubular stockinette, as well as causing other hazards arising from local anomalies in the pressure applied to the limb beneath the tubular stockinette by the inflated cuff and from the increased inflation pressure that may be required in the cuff to stop blood flow.

The pressure applied by a tubular stockinette to a limb of a given shape, circumference and tissue composition can be measured using a biomedical pressure transducer, such as one described by McEwen in U.S. Pat. No. 4,869,265. Using such a transducer, it has been found in tests that pressures from 0 mm Hg to more than 60 mm Hg can be applied to limbs of varying circumferences and physical properties by prior art tubular stockinettes of varying sizes, materials, knits and designs. For comparison, it has been found that an applied pressure as low as 30 mm Hg can partially or completely obstruct venous blood flow, and that applied pressures lower than 60 mm Hg can impede and partially block arterial blood flow. It has been found in tests that the pressure of a snugly applied tourniquet cuff can be as high as 25 mm Hg.

Prior art limb protection sleeves described in U.S. Pat. No. 6,361,548 to McEwen (McEwen '548), U.S. Pat. No. 7,384,425 to McEwen (McEwen '425), and U.S. Pat. No. 7,909,849 to McEwen (McEwen '849), which are incorporated herein by reference, are matched to selected cylindrical tourniquet cuffs so that they apply a safe range of pressures within the circumference range of a selected cylindrical tourniquet cuff.

As the use of surgical tourniquets continues to grow, there is an increasing need to adapt tourniquet cuffs to the different and varying limb shapes encountered across the entire patient population. In some cases, a patient's limb can be generalized as being cylindrical in shape, but in most cases, patients' limbs are more accurately described as being non-cylindrical in shape and tapered, i.e. having a taper when viewed from one end of the area of application (such as the proximal end) to the opposite end (such as the distal end). Contour-type tourniquet cuffs and other approaches are used to adapt the tourniquet cuff to a non-cylindrical limb.

When tubular stockinette such as described in McEwen '548, McEwen '425 and McEwen '849, which has a uniform diameter and uniform stretch properties, is applied to a tapered limb, it can be difficult to achieve an appropriately uniform pressure over the length of the sleeve. The sleeve fits against the limb more tightly at its proximal end than at its distal end, so the portion of the limb within proximal end of the sleeve is subjected to greater pressure. As a result, in many cases the pressure exerted on the limb at the proximal end may exceed a maximum acceptable pressure. At the same time, particularly in the case of a limb having a substantial taper, the pressure exerted on the limb by the sleeve may be too low at the distal end (because the sleeve fits against the limb too loosely). That is, the pressure exerted on the limb by the sleeve at its distal end may be below a minimum acceptable pressure.

In addition, prior art limb protection sleeves may apply excessively high and unsafe pressures to a limb if the practitioner's technique is improper, in the case of soft bandage and cast padding limb protections, or if the practitioner selects an incorrectly matched limb protection sleeve, in the case of matching limb protection sleeves as described in McEwen '548, McEwen '425 and McEwen '849.

Furthermore, to avoid the need to pass the sleeve over the distal end of the limb, which may compromise the surgical site and increase the risk of infection, prior art limb protection sleeves require the use of an instrument (such as shears) to release the sleeve. This process increases perioperative workflow, complexity and time since the practitioner needs to find the appropriate instrument and may struggle with the cutting process while the sleeve is on the patient.

As a result, there is a need for a form of limb protection for use with tourniquet cuffs that overcomes prior art limitations and improves patient safety by: applying uniform pressure to tapered limbs, limiting the maximum pressure applied to the limb, reducing the risk of infection, and reducing perioperative workflow, complexity and time.

SUMMARY

Described below are implementations of a sleeve for use with a tourniquet cuff that addresses some of the drawbacks in the prior art.

According to a first implementation, a sleeve for use with a tourniquet cuff to protect a patient's limb from tourniquet-related injury includes a stretchable body extending longitudinally over a sleeve length between a proximal end and a distal end. The body tapers from the proximal end to the distal end such that a proximal end circumference is greater than a distal end circumference. The body is formed to apply substantially uniform pressure to the patient's limb from the proximal end of the sleeve to the distal end of the sleeve varying only within a predetermined pressure range.

In some implementations, the body has a tubular shape, and the sleeve length is greater than a width of the tourniquet cuff.

In some implementations, the body is formed of a nonwoven material. In some implementations, the body comprises multiple layers, including at least one inner layer and at least one outer layer.

In some implementations, the body comprises circumferentially extending elements at predetermined locations spaced along the sleeve length, the circumferentially extending elements being configured to apply predetermined pressures to the patient's limb. Optionally, the circumferentially extending elements have substantially the same cross-sectional size.

According to another implementation, a tourniquet safety sleeve for use with a tourniquet cuff to reduce injury to a patient's limb comprises a stretchable body and at least one releasable seam. The stretchable body extends longitudinally over a sleeve length between a proximal end and a distal end. The body has a tubular shape, and the sleeve length is sized to be greater than a width of the tourniquet cuff. The at least one releasable seam in the body extends longitudinally between the proximal end and the distal end. The releasable seam is separable upon application of a predetermined force transverse to the releasable seam.

In some implementations, the releasable seam extends substantially linearly between the proximal end and the distal end. In some implementations, the releasable seam comprises at least one discontinuous section. In some implementations, the releasable seam is separable to allow removal of the sleeve from the limb in directions lateral to the limb.

In some implementations, the releasable seam is formed by welding. In some implementations, the releasable seam is configured to have a T-bond extending from at least one end.

The predetermined force upon which the releasable seam is configured to separate can correspond to a predetermined unsafe force exerted by the sleeve radially on the limb. The predetermined safe force can be correlated to a predetermined fit between the limb and the sleeve.

In some implementations, the releasable seam is configured to separate if the limb over which the sleeve is to be extended exceeds a predetermined circumference. In some implementations, the predetermined force upon which the releasable seam is configured to separate is set to allow the seam to be manually released to permit removal of the sleeve from the limb in directions lateral to the limb. In some implementations, the releasable seam comprises a tab formed of a corner of the body adjacent the seam that is folded back against the body.

According to another implementation, a tourniquet cuff and tourniquet cuff protection sleeve assembly comprises a tubular tourniquet cuff and a tourniquet cuff sleeve. The tubular tourniquet cuff is configured for positioning around a limb of a patient. The tourniquet cuff sleeve is configured for positioning around the limb of the patient and between the limb and the tourniquet cuff. The tourniquet cuff sleeve has a sleeve length at least as great as a width of the tourniquet cuff. The tourniquet cuff sleeve is formed of a stretchable nonwoven material and is configured to apply a substantially uniform pressure to the patient's limb along the sleeve length.

The tourniquet cuff sleeve can comprise a releasable seam extending over the sleeve at least partway between a proximal end and a distal end. The substantially uniform pressure applied by the tourniquet cuff sleeve to the limb can be above a predetermined minimum accepted pressure limit and below a maximum accepted pressure limit. The maximum accepted pressure limit can be correlated to a venous occlusion pressure.

The tourniquet cuff sleeve can be tapered from a proximal end to a distal end, and stretch characteristics of the tourniquet cuff sleeve can vary along the sleeve length from lower elasticity adjacent a proximal end to higher elasticity adjacent a distal end. The proximal and/or distal end of the tourniquet cuff sleeve can be relieved to prevent increases in pressure applied to the patient's limb at locations corresponding to the proximal and/or distal end.

The tourniquet cuff sleeve can include markings to indicate the releasable seam. The tourniquet cuff sleeve includes marking to indicate a direction in which the sleeve is configured to be applied over the limb.

According to another implementation, a method of preventing injury to skin and soft tissue of a patient's limb from use of a tourniquet cuff on the limb comprises placing a tourniquet sleeve having a manually releasable seam over the patient's limb at a location where the tourniquet cuff will be applied, the tourniquet sleeve having a tubular body, orienting a manually releasable seam in the tubular body of the tourniquet sleeve for access by a user, placing a tourniquet cuff over the tourniquet sleeve, inflating the tourniquet cuff to apply pressure through the tourniquet sleeve to the patient's limb, deflating the tourniquet cuff, removing the tourniquet cuff from the patient's limb, and manually releasing the tourniquet sleeve from the patient's limb by applying force by hand to tear the manually releasable seam and separate the tourniquet sleeve.

The manually releasing of the tourniquet sleeve can occur without moving the tourniquet sleeve longitudinally along a patient's limb into a surgical field.

The tourniquet sleeve can apply a predetermined pressure to the patient's limb between a minimum acceptable pressure limit and a maximum acceptable pressure limit.

The tourniquet sleeve can have a sleeve taper from a proximal end to a distal end, and the sleeve taper can be selected to accommodate a taper in the patient's limb.

The foregoing and other features and advantages will become more apparent from the following detailed description, which proceeds with reference to the accompanying figures.

BRIEF DESCRIPTION OF THE DRAWINGS

FIGS. 4A, 4B, 4C, 4D and 4E are front elevation, proximal end, distal end, first side elevation and second side elevation views, respectively, of a generally cylindrical sleeve according to a third implementation and shown in a generally flattened state.

FIGS. 4F and 4G are perspective views of the sleeve of FIGS. 4A-4E shown in an expanded state and a generally flattened state, respectively.

FIGS. 5A, 5B, 5C, 5D and 5E are front elevation, proximal end, distal end, first side elevation and second side elevation views, respectively, of a tapered sleeve according to a fourth implementation and shown in a generally flattened state.

FIG. 11A is a schematic diagram showing a tapered sleeve on an idealized tapered limb.

FIG. 11B is a representative graph of the resulting pressures exerted by the tapered sleeve on the tapered limb of FIG. 11A.

FIG. 12A is a schematic diagram of a cylindrical sleeve configured to be non-uniformly stretchable on an idealized tapered limb.

FIG. 12B is a representative graph of the non-uniformly stretchable cylindrical sleeve on the tapered limb of FIG. 12A.

DETAILED DESCRIPTION

Described below are implementations of a tourniquet safety sleeve for reducing limb injury. Tourniquet safety sleeves are designed to be positioned on patients' limbs in the areas over which surgical tourniquet cuffs are applied. Prior exemplary sleeves are described in commonly owned U.S. Pat. Nos. 6,361,548, 7,384,849 and 7,909,849, which are incorporated herein by reference.

Figure 1:
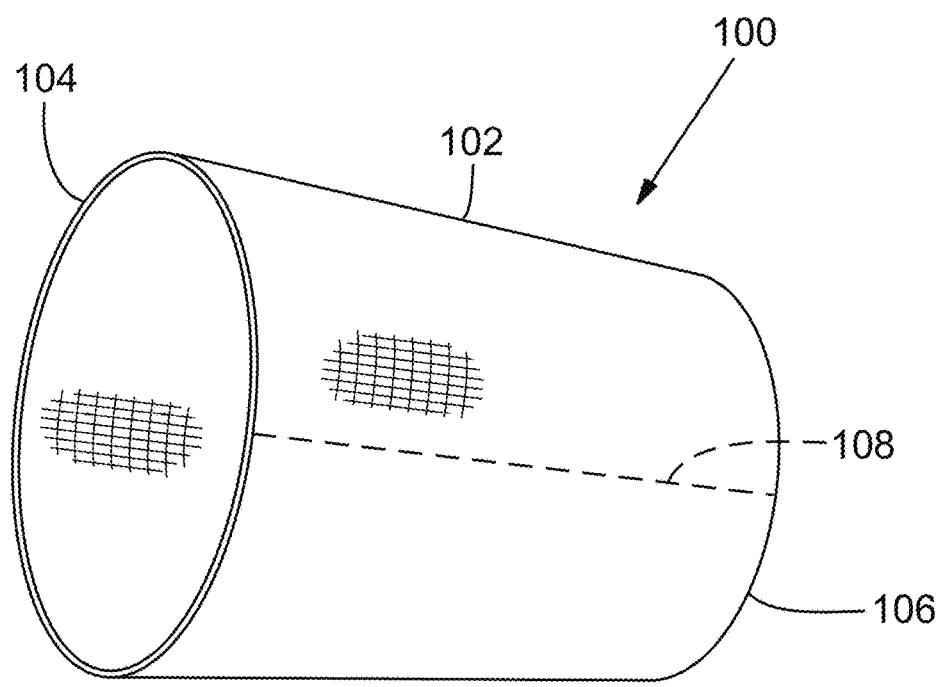
FIG. 1 is a perspective view of a representative sleeve according to a first implementation.
Figure 7:
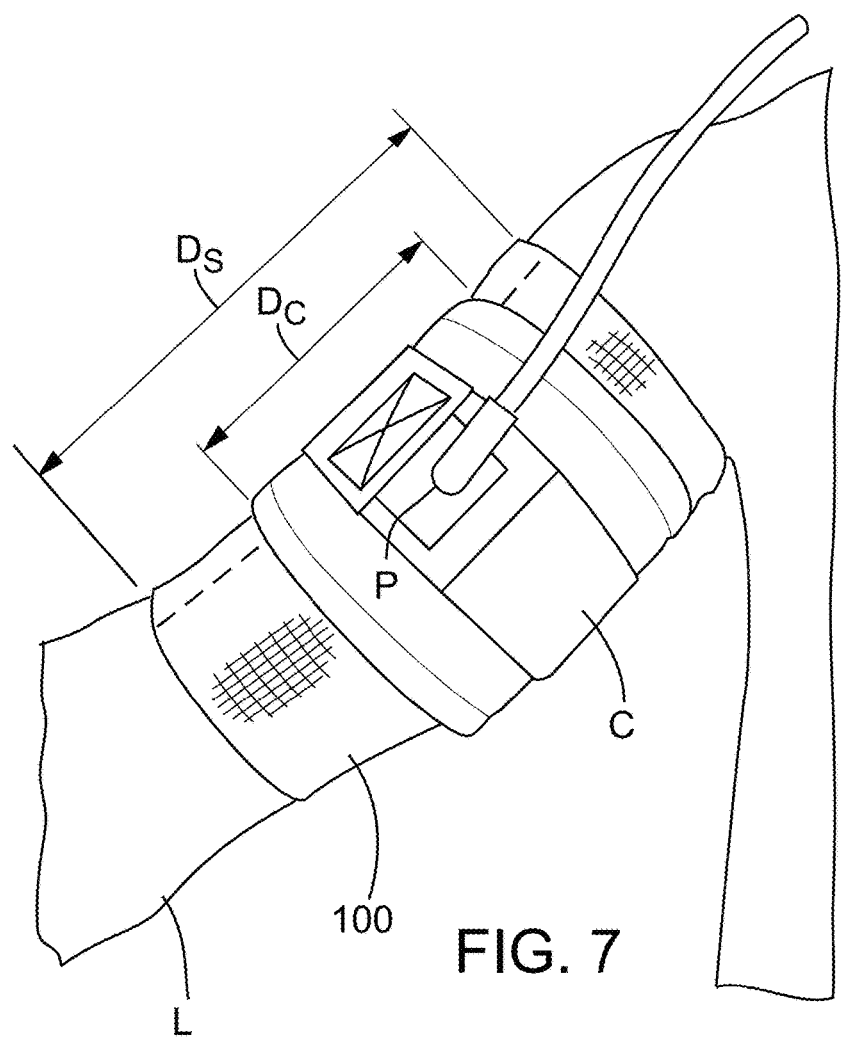
FIG. 7 is a perspective view of a surgical tourniquet cuff on a patient's limb with a sleeve worn in place between the cuff and the limb.

FIG. 1 is a perspective view of a sleeve 100 according to one implementation. The sleeve 100 has a tubular body 102 with a first end 104 (defined as a proximal end) and an opposite second end 106 (defined as a distal end). The proximal and distal ends are defined according to the typical use case where the proximal end of the sleeve is positioned closer to the patient's torso than the distal end, but other use cases are also possible, and the description of the ends as proximal and distal is not intended to be limiting. For context, FIG. 7 is a perspective view of the sleeve 100 shown schematically and in place over a limb L of a patient. A surgical tourniquet cuff C has been wrapped around the sleeve 100 and the limb L, and the ends of the cuff (not shown) have been secured together. The cuff C has a port P that is connected via tubing to a system for controllably inflating and deflating the cuff (not shown). As shown in FIG. 7, the sleeve 100 typically has a dimension $D_S$ measured along the limb (referred to herein as the "length" of the sleeve) that typically exceeds a dimension $D_C$, which is also measured along the limb and is referred to as the "width" of the cuff.

In the implementation illustrated in FIG. 1, the sleeve 100 is tapered from the proximal end 104 to the distal end 106. Alternatively, the sleeve 100 can be configured to have a cylindrical configuration with ends that are substantially equal in size, as is described below, or to have a reverse tapered configuration such that the proximal end is smaller than the distal end. Other geometries are also possible.

Figure 2A:
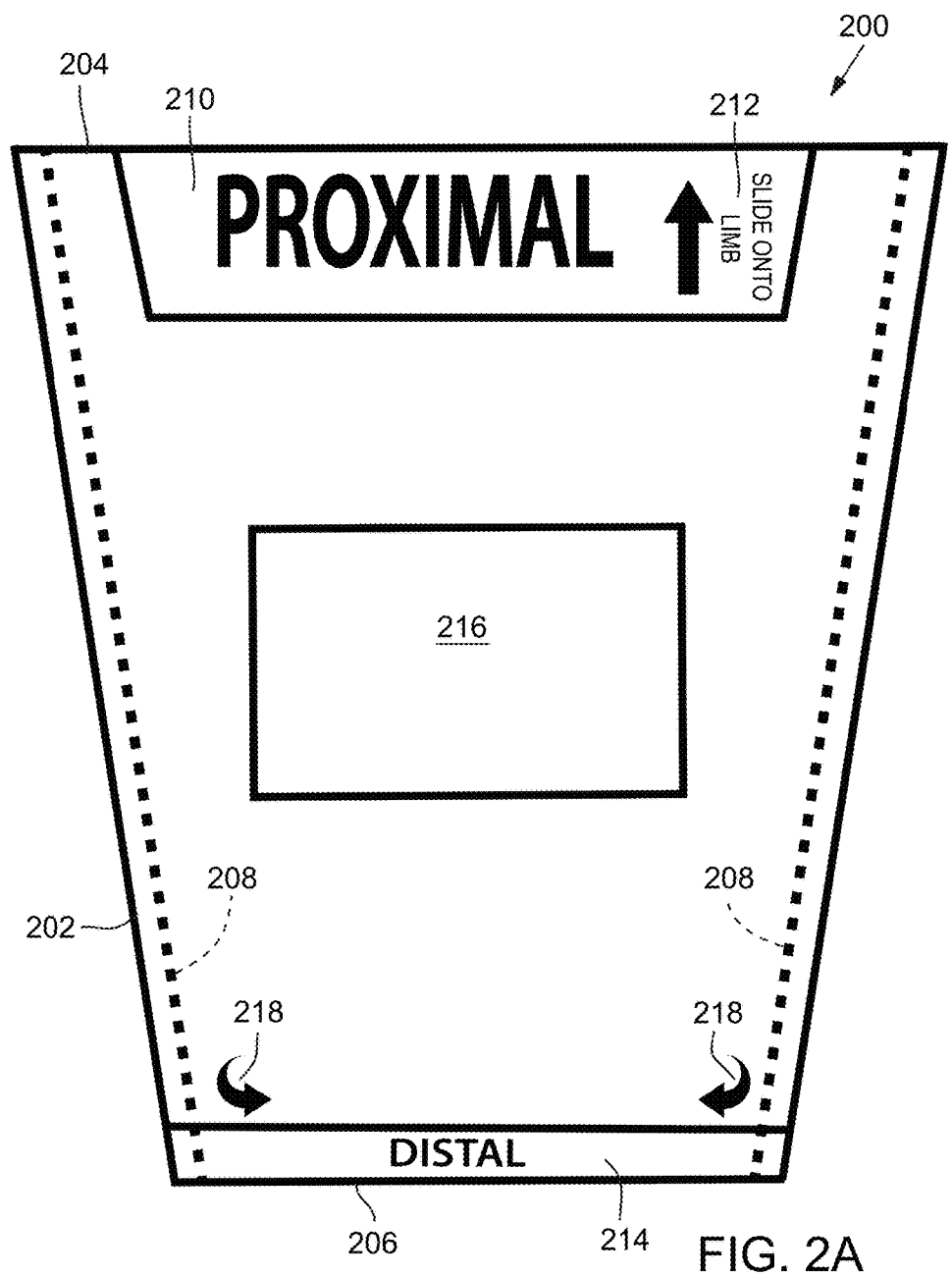
FIG. 2A is a plan view of a sleeve according to a second implementation.

The sleeve 100 may have one or more seams, bonds, welds or other type of junction, such as a longitudinal seam 108 as represented schematically in FIG. 1 (and FIG. 7). In FIG. 1, the seam 108 is a junction where opposite edges of a piece of material are joined together so that the material can have the tubular shape of the body 102 when expanded, such as when it urged over a limb. In other configurations, there may be more than one junction, such as, e.g., two spaced apart seams as shown in FIG. 2A. With two such junctions, it is also possible to form the sleeve from multiple separate pieces of material that are aligned and then joined together. In some implementations, the seam 108 is formed by ultrasonic welding or another similar technique suitable to bond the selected material.

In any of these configurations, it is also possible to form the sleeve so that there are multiple layers, including at least one inner layer and at least one outer layer, as is discussed below in connection with FIG. 3. The inner layer and outer layer may be made of the same material or different materials.

The sleeve 100 is made chiefly of a stretchable, flexible nonwoven material. One such suitable material is available from Haso USA, Inc. (Peachtree Corners, Ga.) under the designation Haso #M-200. Desirably, this non-woven material does not change in width when stretched, unlike some conventional materials. Nonwoven materials, including nonwoven fabrics, include sheet or web structures in which fibers or filaments are bonded together mechanically, thermally and/or chemically. Typically, nonwoven materials do not require any weaving or knitting. Nonwoven materials can be selected for desired properties, including absorbency, liquid repellence, resilience, stretch, softness, strength, flame retardancy, washability, cushioning, insulation, filtration, use as a barrier and/or sterility, to name some examples. In addition, considerations such as bonding, welding or other joining methods, biocompatibility, cost, content and recyclability of can also play a role.

The material(s) of the sleeve 100 can have a repeating pattern, as is described below in greater detail. The sleeve 100 can also be configured to be stretchable in one or more directions. The stretchable quality of the sleeve 100 can be based on the material(s) of which the sleeve is made and/or on additional elements added to impart a desired stretchable quality.

In addition to forming one or more pieces of material into a configuration that can be expanded into a tubular body, the one or more seams can serve other purposes. First, all or part or one or more seams can provide releasable areas of the sleeve. A releasable area is defined as an area on the sleeve that is easier to tear or otherwise separate relative to adjacent areas. The strength of the seam can be controlled by the joining process used to make the seam and the design of the seam. The seam can be configured to separate at predetermined pressures or forces for purposes as described below. In some implementations, all or part of at least one of the seams, or the areas directly adjacent the seams, is a releasable area for the sleeve. In other implementations, the releasable area(s) are located remote from the seam(s).

In one mode, to improve patient safety, the sleeve can be configured to have releasable areas that prevent the sleeve from exerting pressure in excess of a predetermined maximum pressure on the limb. The pressure exerted by the sleeve onto the limb is directly related to the transverse force experienced by the sleeve material as it is stretched. Therefore, the releasable area can be configured to tear, break or otherwise yield, and to release the sleeve if the sleeve applies pressure greater than a predetermined safe maximum pressure. Such a situation could arise if a practitioner attempts to position a sleeve having a designated size range over a limb that exceeds the size range, or if the sleeve is positioned in the incorrect orientation (e.g., proximal and distal ends reversed). Thus, the sleeve could be configured to tear as the practitioner is positioning it, thereby preventing use a sleeve that would exert excessive pressure. The sleeve can be provided with multiple releasable areas, and the different areas can be configured for different purposes.

In addition, or alternatively, the releasable area(s) can allow a practitioner to release the sleeve from the patient's limb, such as by applying a predetermined transverse force to tear the material in the releasable area, generally in a longitudinal direction, to safely separate the sleeve and allow it to be "unrolled" or otherwise removed from the limb in a direction lateral to the limb, rather than requiring the sleeve to be passed over the distal end of the limb in the longitudinal direction. In general, the sleeve is released from the patient's limb at an appropriate time during a procedure, and usually following the removal of the surgical tourniquet in the area where the sleeve was positioned.

By avoiding the need to pass the sleeve over the distal end of the limb, the sleeve can be kept away from the surgical field that is defined to extend beyond the distal end. Desirably, the practitioner can release the sleeve from the patient without the use of an instrument (such as shears), which saves time and effort. Thus, the releasable areas are configured to provide sufficient resistance to release during handling, positioning on a limb and during use under the surgical tourniquet, but can be released manually by a practitioner using a proper technique to allow safe and efficient removal of the sleeve.

Figure 2B:
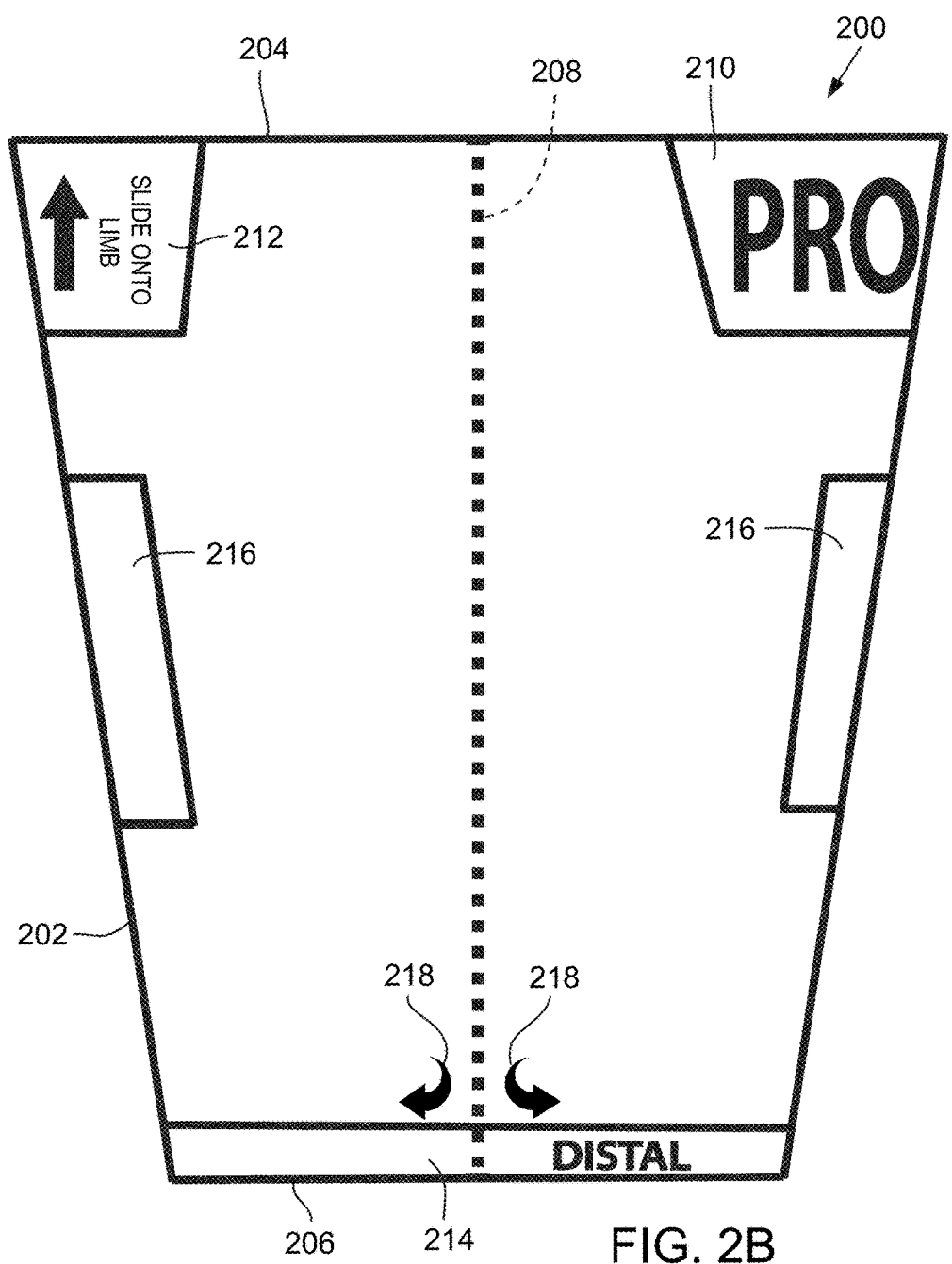
FIG. 2B is a plan view of the sleeve of FIG. 2A that has been rotated to a different position.

In the implementation of FIG. 1 of the sleeve 100, there is one seam or junction 108. In other implementations, two or more pieces of material can be stitched, bonded or otherwise joined together at two or more seams to define the body (see, e.g., FIG. 2A). FIG. 2A is a plan view of a sleeve 200 according to another implementation, shown in a flattened state. FIG. 2B is a plan view similar to FIG. 2A, except the sleeve 200 has been rotated 90 degrees. In the sleeve 200, there are two or more pieces of material joined together at two seams 208 near opposite edges thereof. Of course, it is possible to have multiple seams in in implementations with only a single piece of material.

The sleeve 200 has a tubular body 202 that tapers from a proximal end 204 to a distal end 206 according to a predetermined relationship. Optionally, the sleeve 200 can include one or more of a proximal end marking 210, instructions 212 and/or a distal end marking 214. The proximal end marking 210 indicates the proximal end 204 of the sleeve to a user, such as a medical practitioner. Similarly, the distal end marking 214 indicates the distal end 206 to the practitioner. The proximal end marking 210 and the distal end marking 214 can include text markings as shown, but symbols and/or other indicators (e.g., colors) could also be used.

The instructions 212 can include instructions to the practitioner regarding how to orient and position the sleeve 200. In the illustrated implementation, the instructions "Slide onto limb" with the arrow extending from the proximal end guides a user to expand the flattened sleeve 200 and slide it onto the limb with the proximal end 204 being passed over the distal end of the limb first.

The sleeve 200 can also include one or more other indicia. For example, the sleeve 200 can include indicia 216 positioned approximately midway along the body 202 or in another suitable location. The indicia 216 can include any suitable information, including, e.g., instructional, identification, size and/or origin information for the sleeve 200.

In some implementations, one or more of the seams 208 is configured to be releasable, such as by being tearable or otherwise manually releasable without requiring use of a separate implement (such as shears or another instrument with a blade). In the example of FIGS. 2A and 2B, both of the seams 208 are tearable, and a preferred tearing direction begins at the distal end 206. Optionally, the sleeve 200 may include release instructions 218 to indicate the preferred tearing direction to the practitioner.

Figure 3:
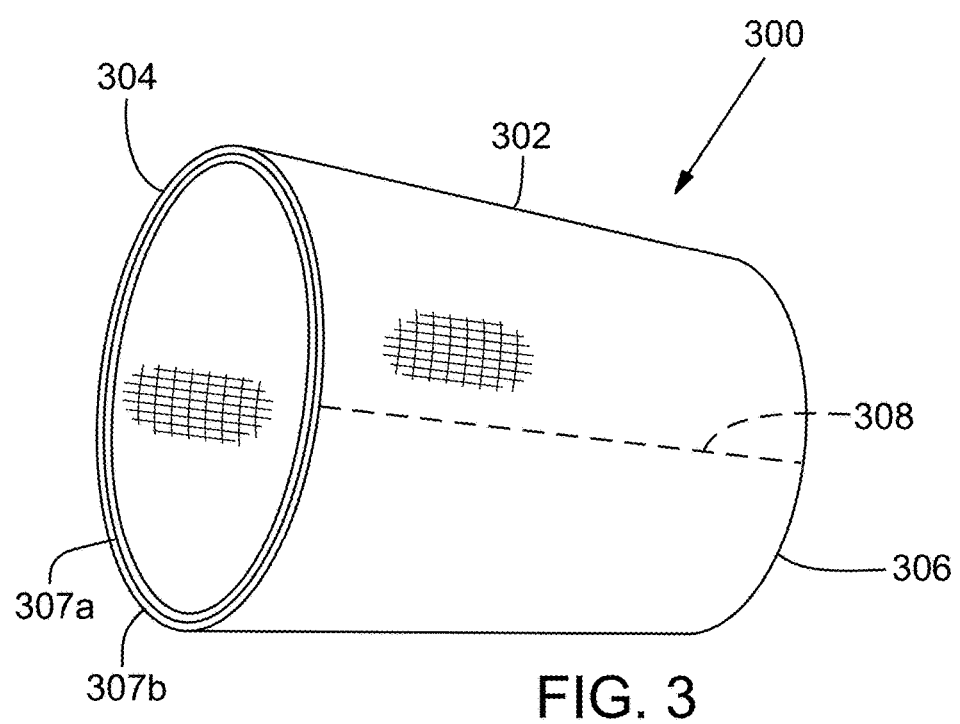
FIG. 3 is a perspective view of a sleeve similar to the sleeve of FIG. 1, but having multiple layers.

FIG. 3 shows a sleeve 300 that is similar to the sleeve 100 having a single seam, but the sleeve 300 is formed of multiple layers of material. Specifically, the body 302 of the sleeve 300 has at least a first inner layer 307a and a second outer layer 307b. The inner layer 307a forms the inner surface of the sleeve 300, which contacts the patient's limb. The outer layer 307b forms the outer surface of the sleeve 300. Although only two layers are shown, using more than two layers is of course possible. The layers 307a, 307b, which may be made of the same material or different materials, may be selected for their respective properties. For example, the layer 307a may be selected to be a softer material that is more comfortable against the patient's skin and tends to prevent injury to the patient. As another example, the layer 307b may be selected to more readily accommodate wrinkles in the cuff because it is in direct contact with an inner surface of the cuff when in use.

In FIG. 3, both of the layers 307a, 307b extend the full length of the sleeve from the proximal end 304 to the distal end 306, but it would also be possible to configure the layers to have lengths (or other geometry) that differ from each other.

FIG. 4A shows a plan view of a sleeve 400 in a generally flattened, relaxed state. FIGS. 4B and 4C show corresponding proximal and distal end views of the sleeve 400, respectively. FIGS. 4D and 4E show corresponding side elevation views, respectively.

The sleeve 400 has a body 402 that is generally cylindrical. As shown, the sleeve 400 has a seam or bond 408 that extends longitudinally, either over the entire length of the sleeve as shown or over a portion of its length. In the illustrated implementation, the seam 408 extends over an area having a transverse width, which is referred to herein as a seam region 410. In some implementations, the seam region 410 can be configured to have a flattened shape and to project radially outwardly from the surface of the cylinder, e.g., as best shown in FIG. 4F. In contrast, the side of body 402 opposite the seam 408 has a smoothly rounded configuration.

As can be seen, the material visible on an outer surface of the sleeve 400 can comprise elements 412 extending transverse to the longitudinal direction that are spaced apart from each other over at least a portion of the body 402, three of which are labeled in the figures. In the illustrated implementation, these elements 412 extend circumferentially around the limb when the sleeve 400 is worn. The elements 412 can be regularly spaced as shown, or spaced at another desired interval. At least some of the elements 412 are elasticized or otherwise configured to stretch. In some of the implementations, all of the elements 412 are elasticized. The elements 412 can be selectively elasticized so that differential pressures are exerted in different longitudinal regions of the sleeve, as described elsewhere herein.

Figure 6:
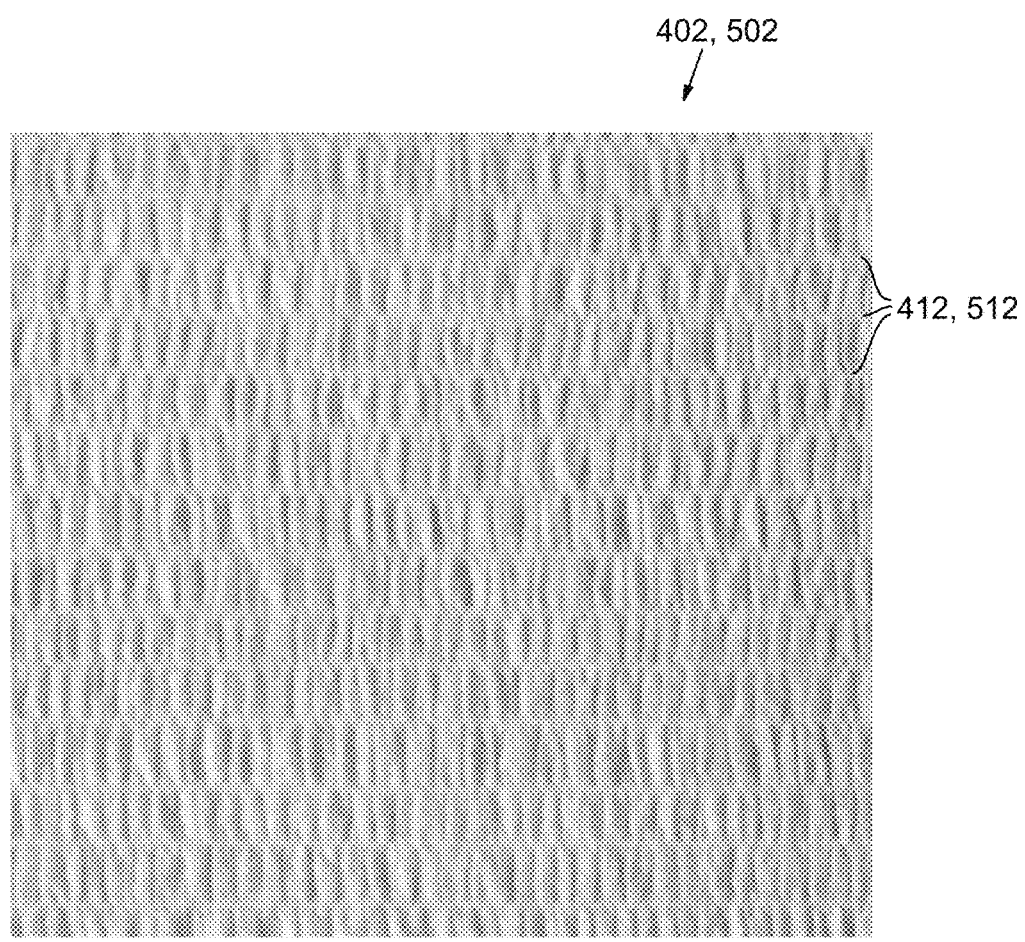
FIG. 6 is a magnified view of a section of the material for the sleeves of FIG. 4A-5E shown in a stretched state.

In the regions between the elements 412, the nonwoven material of the body 402 at rest has an appearance of being shirred or gathered such that the material can expand when the elastic elements 412 are stretched. A section of the Haso #M-200 material stretched from about 14 cm in length to about 22 cm is shown in FIG. 6.

The sleeve 400 can be formed of a single layer of material, or more preferably, of two or more layers of material. As best seen in FIGS. 4B and 4C, the sleeve 400 in the illustrated implementation is formed of two layers of material. At the proximal end as shown in FIG. 4B, the two layers of material have been folded, giving the appearance of only a single layer. At the distal end as shown in FIG. 4C, the two layers of material are visible. It would also be possible to configure the sleeve 400 to have three, four or even more layers of material.

FIG. 4F is a perspective view of the sleeve 400 expanded from its flattened state, such as in preparation for positioning over a limb. FIG. 4F shows the proximal end with one visible layer of material. FIG. 4G is a perspective view of the sleeve 400 in its flattened state and showing the proximal end.

FIG. 5A shows a plan view of a sleeve 500 in a generally flattened, relaxed state. FIGS. 5B and 5C show corresponding proximal and distal end views of the sleeve 500, respectively. FIGS. 5D and 5E show corresponding side elevation views, respectively.

The sleeve 500 has a body 502 that is tapered from the proximal end 520 to the distal end 522. The sleeve 500 has one or more seams or bonds, such as the opposing seams 508a and 508b as shown, which extend along the tapered sides of the body 502, either over the entire length of the sleeve as shown or over a portion of its length. In the illustrated implementation, the seams 508a, 508b extend over respective areas each having a transverse width, which are referred to herein as seam regions 510a, 510b. In some implementations, one or both of the seam regions 510a, 510b can be configured to have a flattened shape and to project radially outwardly from the surface of the cylinder, e.g., similar to the seam region 410 shown in FIG. 4F.

Similar to the sleeve 400, the material visible on an outer surface of the sleeve 500 can comprise elements 512 extending transverse to the longitudinal direction that are spaced apart from each other over at least a portion of the body 502, three of which are labeled in the figures. In the illustrated implementation, these elements 512 extend circumferentially around the limb when the sleeve 500 is worn. The elements 512 can be regularly spaced as shown, or spaced at another desired interval. At least some of the elements 512 are elasticized or otherwise configured to stretch. In some of the implementations, all of the elements 512 are elasticized. The elements 512 can be selectively elasticized so that differential pressures are exerted in different longitudinal regions of the sleeve, as described elsewhere herein.

Similar to the body 402, in the regions between the elements 512, the nonwoven material of the body 502 at rest has an appearance of being shirred or gathered such that the material can expand when the elastic elements 512 are stretched, as shown in FIG. 6.

The sleeve 500 can be formed of a single layer of material, or more preferably, of two or more layers of material. As best seen in FIGS. 5B and 5C, the sleeve 500 in the illustrated implementation is formed of two layers of material. At the proximal end 520 as shown in FIG. 5B, the two layers of material have been folded, giving the appearance of only a single layer. At the distal end 522 as shown in FIG. 5C, the two layers of material are visible. It would also be possible to configure the sleeve 500 to have three, four or even more layers of material. As described, at least some of the circumferential elements 412, 512 are configured to have predetermined properties, such as elasticity, stretch and/or resilience, so that the sleeve in the areas of those elements applies a predetermined pressure to a limb of a predetermined size and shape. For example, one or more of the circumferential elements 412, 512 can be configured to have a predetermined elasticity, and this property can be varied across an array of multiple circumferential elements that are spaced longitudinally from each other. Use of a nonwoven material for the sleeve allows greater flexibility in configuring the material to have specific properties at specific locations than in the case of other materials such as woven or knitted materials. Although the above description refers to the circumferential direction, it would of course be possible to use elements extending at other directions, such as diagonally, to achieve some of the same purposes.

Figure 8A:
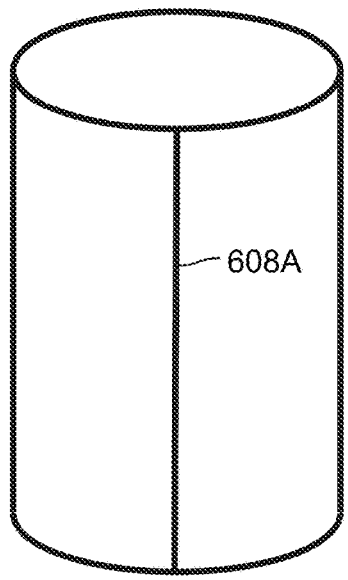
FIG. 8A is a schematic pictorial view of an implementation of the sleeve with a straight seam.
Figure 8B:
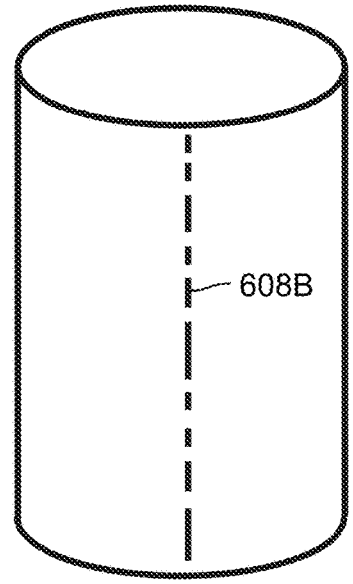
FIG. 8B is a schematic pictorial view of an implementation of the sleeve with a discontinuous seam.
Figure 8C:
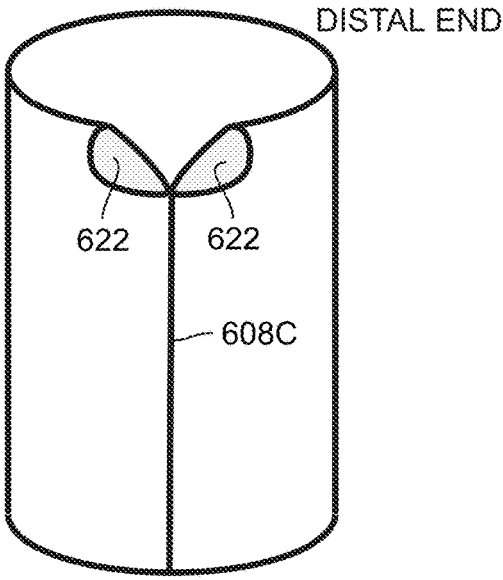
FIG. 8C is a schematic pictorial view of an implementation of the sleeve with a straight seam and an open end.
Figure 8D:
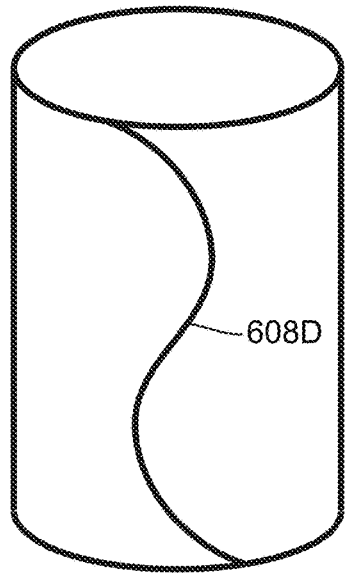
FIG. 8D is a schematic pictorial view of an implementation of the sleeve with a non-linear seam.
Figure 8E:
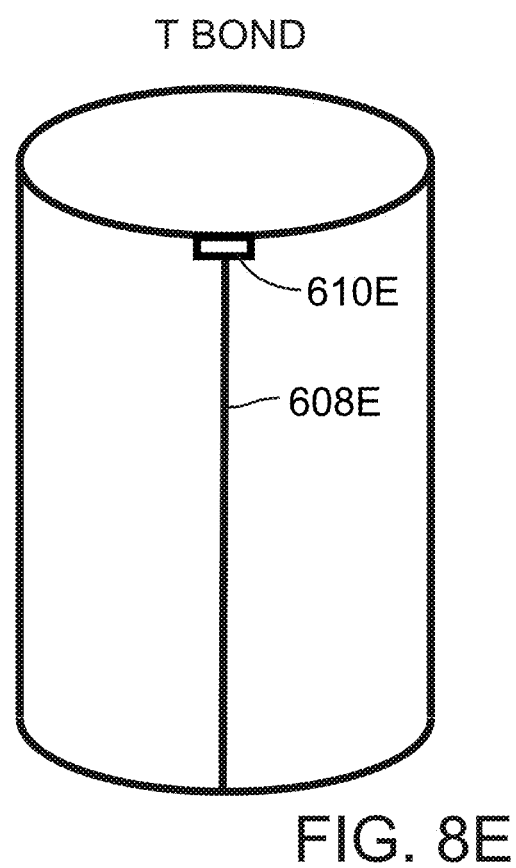
FIG. 8E is a schematic pictorial view of an implementation of the sleeve with a T-bond at a proximal end.

FIGS. 8A-8E show schematic pictorial views of a sleeve with various different seam configurations. In FIG. 8A, the sleeve has a straight seam 608A. In FIG. 8B, the sleeve has a straight seam 608B that is discontinuous. For example, the seam 608B can extend from only one end, or can include segments along its length that are adapted to tear at different forces. In FIG. 8C, the sleeve can be provided with a distal end having a partially open seam 608C. Optionally, the regions of material adjacent the open portion of the seam 608C can form flaps or tabs 622 by which the material can be grasped for tearing or other manipulation. In FIG. 8D, the sleeve can be provided with a longitudinal seam 608D that is curved rather than straight. In FIG. 8E, a seam 608E is configured with a T-bond 610E at one end to increase the seam strength in the region of the T-bond 610E.

Figure 9A:
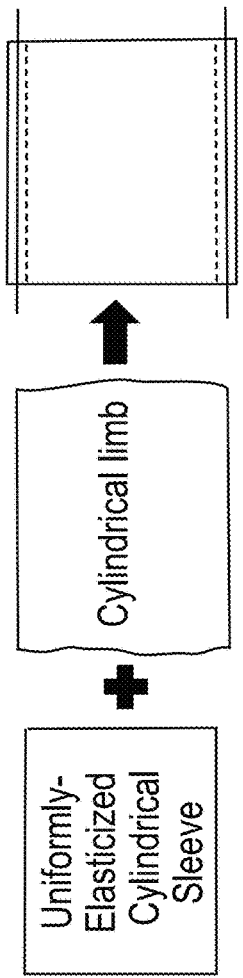
FIG. 9A is a schematic diagram showing a cylindrical sleeve on an idealized cylindrical limb.
Figure 9B:
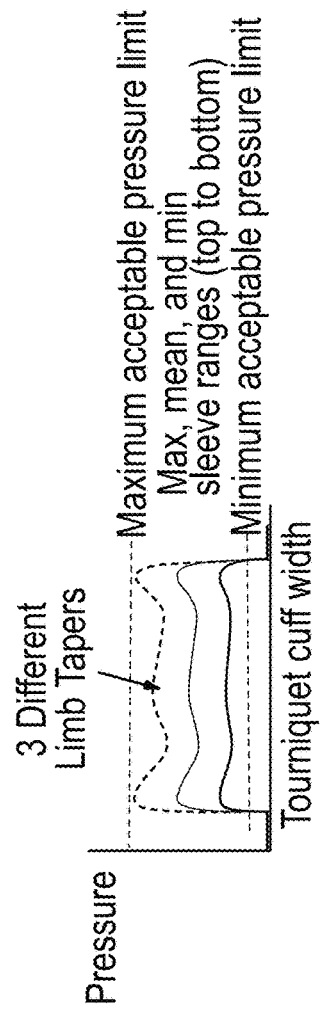
FIG. 9B is a representative graph of the resulting pressures exerted by the cylindrical sleeve on the cylindrical limb the configuration of FIG. 9A.

FIG. 9A is a schematic diagram showing a depiction of a uniformly elasticized sleeve, an idealized cylindrical patient limb, and the resulting configuration when that sleeve is stretched and positioned over the limb. FIG. 9B is a graph showing a maximum acceptable pressure limit and a minimum acceptable pressure limit over the longitudinal dimension of the cuff (sometimes also referred to herein as cuff "width"). FIG. 9B also shows three representative pressure profiles for a given size of sleeve and a limb of (1) maximum size, (2) average size and (3) minimum size, all of which are entirely between the maximum and minimum acceptable pressure limits. The maximum acceptable pressure limit is less than the pressure required for venous occlusion.

Figure 10A:
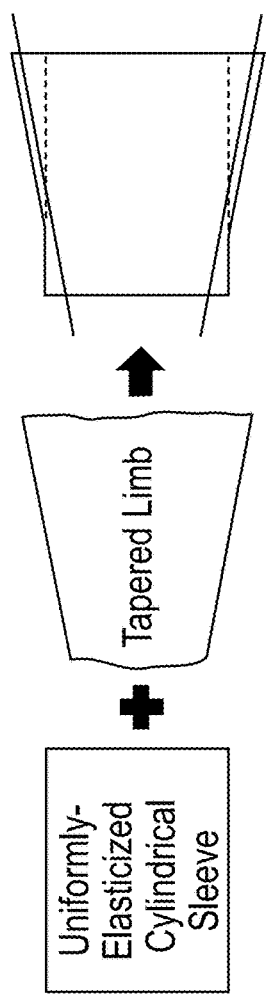
FIG. 10A is a schematic diagram showing a cylindrical sleeve on an idealized tapered limb.
Figure 10B:
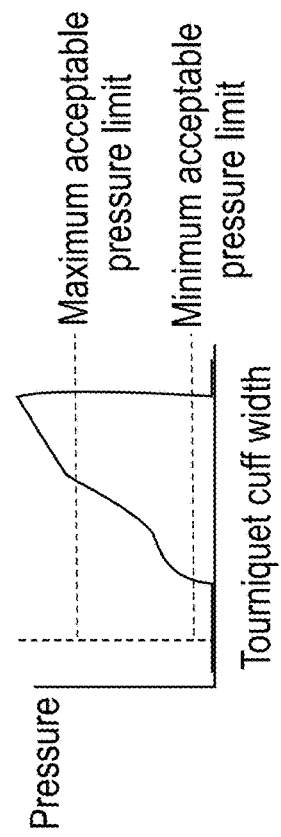
FIG. 10B is a representative graph of the resulting pressures exerted by the cylindrical sleeve on the tapered limb of FIG. 10A.

FIG. 10A is a schematic diagram showing a depiction of a uniformly elasticized cylindrical sleeve, an idealized tapered patient limb, and the resulting configuration when that sleeve is stretched and positioned over the limb. FIG. 10B is a graph showing a maximum acceptable pressure limit and a minimum acceptable pressure limit over the longitudinal dimension of the cuff. In the example, the pressure profile shows that the pressure applied to the limb exceeds the maximum acceptable pressure limit near the proximal end of the sleeve and decreases dramatically until it is less than the minimum acceptable pressure before the distal end of the sleeve.

FIG. 11A is a schematic diagram showing a depiction of a non-cylindrical sleeve of the present invention, an idealized tapered patient limb, and the resulting configuration when that sleeve is stretched and positioned over the limb. FIG. 11B is a graph showing a maximum acceptable pressure limit and a minimum acceptable pressure limit over the longitudinal dimension of the cuff. FIG. 11B also shows three representative pressure profiles for limbs of different tapers, all of which are entirely between the maximum and minimum acceptable pressure limits. Furthermore, the applied pressure under the tourniquet cuff, from the proximal end to the distal end of the sleeve is substantially uniform, resulting in optimal limb protection.

FIG. 12A is a schematic diagram showing a depiction of a non-uniformly elasticized cylindrical sleeve of the present invention, an idealized tapered patient limb, and the resulting configuration when that sleeve is stretched and positioned over the limb. The non-uniformly elasticized, or varyingly resilient, sleeve is configured to have a proximal segment of low elasticity, an intermediate segment of medium elasticity and a distal segment of high elasticity such that when applied to a non-cylindrically shaped limb, the pressure exerted by the sleeve is substantially uniform between the proximal and distal ends. FIG. 12B is a graph showing a maximum acceptable pressure limit and a minimum acceptable pressure limit over the longitudinal dimension of the cuff. FIG. 12B also shows three representative pressure profiles for limbs of three different tapers, all of which are entirely between the maximum and minimum acceptable pressure limits. Furthermore, the applied pressure under the tourniquet cuff, from the proximal end to the distal end of the sleeve is substantially uniform, resulting in optimal limb protection.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A sleeve for use with a tourniquet cuff to protect a patient's limb from tourniquet-related injury, the sleeve comprising:
   a stretchable body extending longitudinally over a sleeve length between a proximal end and a distal end, the body having a tubular shape and the sleeve length configured to be greater than a longitudinal dimension of a tourniquet cuff to be applied over the sleeve, wherein the body tapers from the proximal end to the distal end such that a proximal end circumference is greater than a distal end circumference,
   wherein the body is formed of a nonwoven material comprising at least one inner layer and one outer layer, the body being configured to apply substantially uniform pressure to the patient's limb from the proximal end of the sleeve to the distal end of the sleeve varying only within a predetermined pressure range;
   wherein the body comprises circumferentially extending elements at predetermined locations spaced along the sleeve length, the circumferentially extending elements being configured such that the body applies the substantially uniform pressure that varies only within the predetermined pressure range to the patient's limb along the sleeve length; and
   at least one single-use releasable weld in the body extending longitudinally between the proximal end and the distal end, wherein the single-use releasable weld is configured to separate if the sleeve is positioned over a limb having a limb circumference that exceeds a predetermined limb circumference size range of the sleeve.

2. The sleeve of claim 1, wherein the single-use releasable weld extends substantially linearly in the body between the proximal end and the distal end.

3. The sleeve of claim 1, wherein the single-use releasable weld is configured to separate if a pressure exerted on the limb over which the sleeve is positioned reaches a venous occlusion pressure.

4. The sleeve of claim 1, wherein the single-use releasable weld is manually tearable to permit removal of the sleeve from the limb in directions lateral to the limb.

5. The sleeve of claim 1, wherein the substantially uniform pressure applied by the sleeve to the limb is above a predetermined minimum accepted pressure limit and below a maximum accepted pressure limit.

6. The sleeve of claim 1, wherein stretch characteristics of the sleeve vary along the sleeve length from lower elasticity adjacent a proximal end to higher elasticity adjacent a distal end.

7. The sleeve of claim 1, further comprising at least one marking on the sleeve indicating a direction in which the sleeve is to be applied over the limb.

8. The sleeve of claim 1, further comprising at least one marking on the sleeve indicating a preferred direction by which to separate the single-use releasable weld to allow removal of the sleeve from the limb.

9. A sleeve for use with a tourniquet cuff to protect a patient's limb from tourniquet-related injury, the sleeve comprising:
   a stretchable body extending longitudinally over a sleeve length between a proximal end and a distal end, the body having a tubular shape and the sleeve length configured to be greater than a longitudinal dimension of a tourniquet cuff to be applied over the sleeve, wherein the body tapers from the proximal end to the distal end such that a proximal end circumference is greater than a distal end circumference,
   wherein the body is formed of a nonwoven material comprising at least one inner layer and one outer layer, the body being configured to apply substantially uniform pressure to the patient's limb from the proximal end of the sleeve to the distal end of the sleeve varying only within a predetermined pressure range;
   wherein the body comprises circumferentially extending elements at predetermined locations spaced along the sleeve length, the circumferentially extending elements being configured such that the body applies the substantially uniform pressure that varies only within the predetermined pressure range to the patient's limb along the sleeve length;
   at least one single-use releasable weld in the body extending longitudinally between the proximal end and the distal end, wherein the single-use releasable weld is configured to separate if the sleeve is positioned over a limb having a limb circumference that exceeds a predetermined limb circumference size range of the sleeve; and
   at least one marking on the sleeve indicating a transverse direction in which to apply force manually to separate the single-use releasable weld.

10. A sleeve for use with a tourniquet cuff to protect a patient's limb from tourniquet-related injury, the sleeve comprising:
   a stretchable body extending longitudinally over a sleeve length between a proximal end and a distal end, the body having a tubular shape and the sleeve length configured to be greater than a longitudinal dimension of a tourniquet cuff to be applied over the sleeve, wherein the body tapers from the proximal end to the distal end such that a proximal end circumference is greater than a distal end circumference,
   wherein the body is formed of a nonwoven material comprising at least one inner layer and one outer layer, the body being configured to apply substantially uniform pressure to the patient's limb from the proximal end of the sleeve to the distal end of the sleeve varying only within a predetermined pressure range;
   wherein the body comprises circumferentially extending elements at predetermined locations spaced along the sleeve length, the circumferentially extending elements being configured such that the body applies the substantially uniform pressure that varies only within the predetermined pressure range to the patient's limb along the sleeve length;
   at least one single-use releasable weld in the body extending longitudinally between the proximal end and the distal end and configured to separate upon application of a predetermined force transverse to the single-use releasable weld;
   at least one first marking on the sleeve indicating a direction in which the sleeve is to be applied over the limb; and
   at least one second marking on the sleeve indicating a transverse direction in which to apply force manually to separate the single-use releasable weld.

* * * * *